United States Patent
Peters et al.

(10) Patent No.: US 11,660,052 B2
(45) Date of Patent: May 30, 2023

(54) VITAL SIGNS MONITORING SYSTEM AND METHOD

(71) Applicant: Robert Bosch GmbH, Stuttgart (DE)

(72) Inventors: Christian Peters, Sunnyvale, CA (US); Mohak Shah, Dublin, CA (US); Zubin Abraham, Sunnyvale, CA (US); Thomas Rocznik, Mountain View, CA (US); Seow Yuen Yee, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 280 days.

(21) Appl. No.: 16/954,600

(22) PCT Filed: Nov. 8, 2018

(86) PCT No.: PCT/EP2018/080664
§ 371 (c)(1),
(2) Date: Jun. 17, 2020

(87) PCT Pub. No.: WO2019/092133
PCT Pub. Date: May 16, 2019

(65) Prior Publication Data
US 2020/0330050 A1    Oct. 22, 2020

Related U.S. Application Data

(60) Provisional application No. 62/583,754, filed on Nov. 9, 2017.

(51) Int. Cl.
*A61B 5/00*      (2006.01)
*G16H 50/20*     (2018.01)
(Continued)

(52) U.S. Cl.
CPC .......... *A61B 5/7278* (2013.01); *A61B 5/0205* (2013.01); *A61B 5/02028* (2013.01);
(Continued)

(58) Field of Classification Search
CPC . A61B 5/7278; A61B 5/02028; A61B 5/0205; A61B 5/7203; A61B 5/0002;
(Continued)

(56) References Cited

U.S. PATENT DOCUMENTS

2011/0066042 A1* 3/2011 Pandia ................. A61B 5/7207
                                                  600/513
2012/0123232 A1* 5/2012 Najarian .............. A61B 5/0022
                                                  600/407
(Continued)

FOREIGN PATENT DOCUMENTS

WO      2017/174814 A1    10/2017

OTHER PUBLICATIONS

Klabunde, Cardiovascular Physiology Concepts, Jul. 3, 2015, CV Physiology (https://www.cvphysiology.com/Heart%20Disease/HD010), accessed Mar. 23, 2022. (Year: 2015).*
(Continued)

*Primary Examiner* — Joseph M Dietrich
*Assistant Examiner* — Michael T. Holtzclaw
(74) *Attorney, Agent, or Firm* — Maginot, Moore & Beck LLP

(57) ABSTRACT

A vital signs monitoring system includes a peak pattern detection module configured to output a peak prediction signal from sensor signals based on a peak prediction algorithm; a vital sign estimating module configured to estimate a vital sign based on the peak prediction signal; an activity and context detector module configured to output a context signal based on at least one environmental condition and/or activity level of the person; and a concept drift detection module configured to output a drift signal based on drift detected in the estimated vital sign. The peak pattern
(Continued)

prediction module is configured to update the peak prediction algorithm based on the context signal and the drift signal.

14 Claims, 14 Drawing Sheets

(51) Int. Cl.
```
G16H 40/60      (2018.01)
A61B 5/02       (2006.01)
A61B 5/0205     (2006.01)
A61B 5/021      (2006.01)
A61B 5/024      (2006.01)
A61B 5/11       (2006.01)
A61B 5/318      (2021.01)
```
(52) U.S. Cl.
CPC .......... *A61B 5/7203* (2013.01); *G16H 40/60* (2018.01); *G16H 50/20* (2018.01); *A61B 5/0002* (2013.01); *A61B 5/021* (2013.01); *A61B 5/02416* (2013.01); *A61B 5/1102* (2013.01); *A61B 5/1118* (2013.01); *A61B 5/318* (2021.01); *A61B 2560/0223* (2013.01); *A61B 2560/0242* (2013.01); *A61B 2562/0219* (2013.01)

(58) Field of Classification Search
CPC ... A61B 5/021; A61B 5/02416; A61B 5/1102; A61B 5/1118; A61B 5/318; A61B 2560/0223; A61B 2560/0242; A61B 2562/0219; A61B 5/349; A61B 5/02125; A61B 5/7246; G16H 40/60; G16H 50/20; G16H 40/40; G16H 50/30
See application file for complete search history.

(56) References Cited

U.S. PATENT DOCUMENTS

| | | | |
|---|---|---|---|
| 2015/0374240 | A1* | 12/2015 | Lee ................. A61B 5/7278 600/483 |
| 2016/0029966 | A1* | 2/2016 | Salas-Boni ........ A61B 5/02055 600/347 |
| 2018/0279953 | A1* | 10/2018 | Wang .................... A61B 5/1118 |

OTHER PUBLICATIONS

International Search Report and Written Opinion corresponding to PCT Application No. PCT/EP2018/080664, dated Mar. 1, 2019 (12 pages).
Yu, Shujian et al., "Concept Drift Detection with Hierarchical Hypothesis Testing," Proceedings of the 2017 SIAM International Conference on Data Mining, Jun. 30, 2017, pp. 768-776, Society for Industrial and Applied Mathematics, Philadelphia, PA.

* cited by examiner

Algorithm II: Peek pattern detection module

Input: Data stream $\{(X_t, Y_t^{ACD}, Y_t^{CDD}, M_t)\}_{t=0}^{\infty}$ where $X_t \in \mathbb{R}^d$ are the sensor readings from accelerometers, ECG, etc. and $M_t \in \mathbb{R}$ is the calibration and memory data, activity and context detector module output ($Y_t^{ACD}$), concept drift detector output ($Y_t^{CDD}$), predefined parameter ($i$), mode ($m$), sample rate (SR), users heart rate $\widetilde{HR}$, $\delta$ is $>2$ and represents the expected frequency of the mass transit time (MTT).

Output: Peak pattern detection module output ($Y_t^{PPD}$),
1: Initialize:
   $Y_t^{PPD} \leftarrow$ Null,
2:    for $t = 1$ to $\infty$ do
3:      *compute* $\rho(z), \rho(x)$
4:      if ($M_t^i \neq$ Null)
5:        $i \leftarrow M_t^i$,
6:      end if
7:      if ($Y_t^{CDD} \neq$ Null)
8:        $m \leftarrow Y_t^{CDD}$
9:        Reinitialize M,
10:     end if
11:     if $(P(\rho_{t-\Delta}(z)) > \tau) \& (P(\rho_t(x)) > \tau) \& (\Delta \sim \frac{\widetilde{HR} \cdot SR}{60 \cdot \delta})$
12:        $Y_{t-\Delta}^{z1} \leftarrow 1$
          $Y_t^x \leftarrow 1$
13:        if $(P(\rho_{t-\Delta 2}(z)) > \tau 2) \& (\Delta_2 < \Delta)$
14:          $Y_{t-\Delta 2}^{z2} \leftarrow 1$
15:        else
16:          $Y_{t-\Delta 2}^{z2} \leftarrow 0$
17:        end if
18:     else
19:        $Y_{t-\Delta}^{z1} \leftarrow 0$
          $Y_{t-\Delta 2}^{z2} \leftarrow 0$
          $Y_t^x \leftarrow 0$
20:     end if
21:     $Y_t^{PPD} \leftarrow \{Y_{t-\Delta}^{z1}, Y_{t-\Delta 2}^{z2}, Y_t^x\}$
22:    end for

FIG. 11

Algorithm III: Concept drift detection module

Input: Data stream $\{(X_t, Y_t^{PPD}, M_t)\}_{t=0}^{\infty}$ where $X_t \in \mathbb{R}^d$ are the sensor readings from environmental sensors, ECG, etc. and $M_t \in \mathbb{R}$ is the calibration and memory data, peak pattern detector output ($Y_t^{PPD}$), predefined parameter ($i$), Time decaying factor $\eta_*$; Warning significance level $\delta_*$; Detect significance level $\epsilon_*$. $\widehat{f}_1$ is a function of $X_t$ and $\widehat{f}_2$ is either a function of ECG signal or an orthogonal function of $\widehat{f}_1$.

Output: Concept drift detection module output ($Y_t^{CDD}$),
1: Initialize:
    $Y_t^{CDD} \leftarrow \text{Null}, \dot{y}_1 \leftarrow 0, \dot{y}_2 \leftarrow 0, \dot{c}_1 \leftarrow 0, \dot{c}_2 \leftarrow 0,$
    confusion matrix $C^{(0)} \leftarrow [1,1;1,1]; R_*^{(0)} \leftarrow 0.5,$
2:   for $t = 1$ to $\infty$ do
3:     if $(\widehat{f}_1(X_t) == 1)$, do  $\dot{y}_1 \leftarrow 1$, end if
      if $(\widehat{f}_2(X_t) == 1)$, do  $\dot{y}_2 \leftarrow 1$, end if
4:     $\hat{y}_1 \leftarrow \max(\widehat{f}_1(X_t), \dot{y}_1)$
      $\hat{y}_2 \leftarrow \max(\widehat{f}_2(X_t), \dot{y}_2)$
      $\dot{c}_1 \leftarrow \dot{c}_1 + 1; \quad \dot{c}_2 \leftarrow \dot{c}_2 + 1;$
      if $(\dot{c}_1 == i)$, Then  $\dot{y}_1 \leftarrow 0,$ end if
      if $(\dot{c}_2 == i)$, Then  $\dot{y}_2 \leftarrow 0,$ end if
5     $C^{(t)}[\hat{y}_1][\hat{y}_2] \leftarrow C^{(t-1)}[\hat{y}_1][\hat{y}_2] + 1$
6:     for each $* \in \{TPR, TNR, PPV, NPV\}$ do
        if ($*$ is influenced by $(y_t, \hat{y}_t)$) do
7:         $R_*^{(t)} \leftarrow \eta_* R_*^{(t-1)} + (1 - \eta_*) \mathbf{1}_{\{y_t = \hat{y}_t\}}$
8:       else
9:         $R_*^{(t)} \leftarrow \eta_* R_*^{(t-1)}$
10:     end if
20:     if $((\exists R_*^{(t)} > \delta_*^t) \,\&\, time = 0)$ do
22:       $time \leftarrow t$
23:     else if $(\nexists R_*^{(t)} > \delta_*^t)$ do
24:       $time \leftarrow 0$
25:     end if
26:     if $(\exists R_*^{(t)} > \epsilon_*^t)$ do
30:       $Y_t^{CDD} \leftarrow \{t, time\}$
31:       $M_t^{CDD} \leftarrow \{t, time\}$
32:     end if
33:   end for

FIG. 12

Algorithm IV: Activity and environmental context drift module

Input: Data stream $\{(X_t, M_t, U_t)\}_{t=0}^{\infty}$ where $X_t \in \mathbb{R}^d$ are the sensor readings from accelerometers, ECG, etc. and $M_t \in \mathbb{R}$ is the calibration and memory data, $U_t \in \mathbb{R}$ is the calibration and memory data, predefined parameter $(i)$, Time decaying factor $\eta_*$; Warning significance level $\delta_*$; Detect significance level $\epsilon_*$. $\widehat{f}_1$ and $\widehat{f}_2$ are orthogonal function of $X_t$

Output: Concept drift detection module output ($Y_t^{ACD}$).
1: Initialize:
   $Y_t^{ACD} \leftarrow \text{Null}, \dot{y}_1 \leftarrow 0, \dot{y}_2 \leftarrow 0, \dot{c}_1 \leftarrow 0, \dot{c}_2 \leftarrow 0$,
   confusion matrix $C^{(0)} \leftarrow [1,1;1,1]; R_*^{(0)} \leftarrow 0.5$.
2:    for $t = 1$ to $\infty$ do
3:      if ($U_t = Null$)
4:        if ($\widehat{f}_1(X_t) == 1$), do   $\dot{y}_1 \leftarrow 1$, end if
           if ($\widehat{f}_2(X_t) == 1$), do   $\dot{y}_2 \leftarrow 1$, end if
           $\hat{y}_1 \leftarrow \max(\widehat{f}_1(X_t), \dot{y}_1)$
           $\hat{y}_2 \leftarrow \max(\widehat{f}_2(X_t), \dot{y}_2)$
           $\dot{c}_1 \leftarrow \dot{c}_1 + 1; \quad \dot{c}_2 \leftarrow \dot{c}_2 + 1;$
           if ($\dot{c}_1 == i$), Then   $\dot{y}_1 \leftarrow 0$, end if
           if ($\dot{c}_2 == i$), Then   $\dot{y}_2 \leftarrow 0$, end if
5           $C^{(t)}[\hat{y}_1][\hat{y}_2] \leftarrow C^{(t-1)}[\hat{y}_1][\hat{y}_2] + 1$
6:       for each $* \in \{TPR, TNR, PPV, NPV\}$ do
             if ($*$ is influenced by $(y_t, \hat{y}_t)$) do
7:                $R_*^{(t)} \leftarrow \eta_* R_*^{(t-1)} + (1-\eta_*) \mathbf{1}_{\{y_t = \hat{y}_t\}}$
8:           else
9:                $R_*^{(t)} \leftarrow \eta_* R_*^{(t-1)}$
10:          end if
20:          if $((\exists R_*^{(t)} > \delta_*^t)$ & $time = 0)$ do
22:             $time \leftarrow t$
23:          else if ($\nexists R_*^{(t)} > \delta_*^t$) do
24:             $time \leftarrow 0$
25:          end if
26:          if ($\exists R_*^{(t)} > \epsilon_*^t$) do
30:             $Y_t^{ACD} \leftarrow \{t, time, R_*^{(t)}\}$
31:             $M_t^{ACD} \leftarrow \{t, time, R_*^{(t)}\}$
32:          end if
33:      else
34:          $Y_t^{ACD} \leftarrow \{t, time, U_t\}$
35:          $M_t^{ACD} \leftarrow \{t, time, U_t\}$
36:      end if
33:    end for

FIG. 13

Algorithm I: Adaptive Blood Pressure Estimator

Input: Data stream $\{(X_t, M_t)\}_{t=0}^{\infty}$ where $X_t \in \mathbb{R}^d$ are the sensor readings from accelerometers, ECG, etc. and $M_t \in \mathbb{R}$ is the calibration and memory data.

Output: Blood pressure estimator ($Y_t^{BPE}$), peak pattern detection module output ($Y_t^{PPD}$), activity and context detector module output ($Y_t^{ACD}$), concept drift detector output ($Y_t^{CDD}$).

1: Initialize:
　　$Y_t^{BPE} \leftarrow$ Null, $Y_t^{PPD} \leftarrow$ Null, $Y_t^{ACD} \leftarrow$ Null, $Y_t^{CCD} \leftarrow$ Null
2: 　for $t = 1$ to $\infty$ do
3: 　　　$Y_t^{ACD} \leftarrow$ ACD $((X_t, M_t))$
4: 　　　if $(Y_t^{ACD} \neq$ Null$)$
5: 　　　　Reinitialize M
6: 　　　end if
7: 　　　$Y_t^{CDD} \leftarrow$ CDD $((X_t, Y_t^{PPD}, M_t))$
8: 　　　if $(Y_t^{CCD} \neq$ Null$)$
9: 　　　　Reinitialize M, PPD
10: 　　　end if
11: 　　　$Y_t^{PPD} \leftarrow$ PPD $((X_t, Y_t^{ACD}, Y_t^{CDD}, M_t))$
12: 　　　$Y_t^{BPE} \leftarrow$ BPE $((Y_t^{PPD}, M_t))$
13: 　end for

FIG. 14

VITAL SIGNS MONITORING SYSTEM AND METHOD

CROSS-REFERENCE TO RELATED APPLICATIONS

This application is a 35 U.S.C. § 371 National Stage Application of PCT/EP2018/080664, filed on Nov. 8, 2018, which claims priority to U.S. Provisional Application Ser. No. 62/583,754, filed on Nov. 9, 2017, the disclosures of which are incorporated herein by reference in their entirety.

TECHNICAL FIELD

This disclosure is related to health monitoring devices, and more particularly, to vital signs monitoring systems and methods.

BACKGROUND

Blood pressure (BP) is an important indicator of cardiovascular health and other physiological conditions. Blood pressure may be measured with conventional methods on an infrequent basis in a medical setting. However, there are also needs to measure blood pressure on a more frequent basis and under various conditions outside of the medical setting. For instance, certain blood pressure dynamics, e.g., the non-dipper blood pressure pattern, when a person is sleeping, are of medical importance. Such dynamics are not easily measurable with conventional methods. Moreover, for example, blood pressure variations during daily activities after certain medications are consumed may be used to optimize medical treatments.

SUMMARY

In accordance with one embodiment of the present disclosure, a vital signs monitoring system configured to be worn or carried on a body of a person is provided. The vital signs monitoring system includes at least one sensor configured to detect at least one vital sign parameter in a person and to output sensor signals indicative of the at least one vital sign parameter, and an adaptive vital sign estimating system. The adaptive vital sign estimating system includes a peak pattern detection module configured to detect a peak pattern in the sensor signals and to output a peak prediction signal according to a peak prediction algorithm; a vital sign estimating module configured to estimate a vital sign based on the peak pattern detected by the peak pattern detection module; an activity and context detector module configured to detect changes in environmental conditions and activity levels of the person and to output a context signal to the peak pattern detection module, the peak pattern detection module being configured to update the peak prediction algorithm based on the context signal; and a concept drift detection module configured to detect drift in the estimated vital sign and to output a drift signal to the peak pattern detection module, the peak pattern detection module being configured to update the peak prediction algorithm based on the drift signal.

In accordance with another embodiment of the present disclosure, a method of monitoring vital signs of a person is provided. The method includes detecting at least one vital sign parameter in the person using at least one sensor; generating a peak prediction signal based on the detected vital sign parameter according to a peak prediction algorithm using a processor; estimating a vital sign of the person based on the peak prediction signal; outputting an estimated vital sign signal; generating a context signal indicative of at least one environmental condition and/or activity level detected; generating a drift signal indicative of drift detected in the estimated vital sign signal; and updating the peak prediction algorithm based on the context signal and the drift signal using the processor.

In embodiments, the drift signal may be provided to a sensor calibration system that is configured to calibrate the at least one sensor based on the drift signal.

In embodiments, the activity and context detection module is configured to receive input via a user interface indicating at least one environmental condition or activity level.

In embodiments, the vital sign monitored by the system is blood pressure. The at least one sensor may comprise one or more accelerometers.

In embodiments, the at least one sensor is configured to detect at least one or more of electrocardiogram (ECG) signal, a first motion signal, a second motion signal, a photoplethysmorgram (PPG) signal, seismocardiogram signal (SCG) and ballistocardiogram (BCG) signal.

In embodiments, the peak pattern detection module is configured to identify peaks indicating exact timestamps when the heart of the person contracts and/or when blood rushes through the Aorta of the heart.

In embodiments, the concept drift detection module is configured to detect drift using a hierarchal linear four rates approach.

BRIEF DESCRIPTION OF THE DRAWINGS

These and other features, aspects, and advantages of this disclosure will become better understood when the following detailed description of certain exemplary embodiments is read with reference to the accompanying drawings in which like characters represent like arts throughout the drawings, wherein:

FIG. 11 is a depiction of an exemplary which may be implemented in the peak pattern detection module of the system of FIG. 5.

FIG. 12 is a depiction of an exemplary which may be implemented in the concept drift detection module of the system of FIG. 5.

FIG. 13 is a depiction of an exemplary which may be implemented in the activity and context detection module of the system of FIG. 5.

FIG. 14 is a depiction of an exemplary which may be implemented in the blood pressure estimating module of the system of FIG. 5.

DETAILED DESCRIPTION

Figure 1:
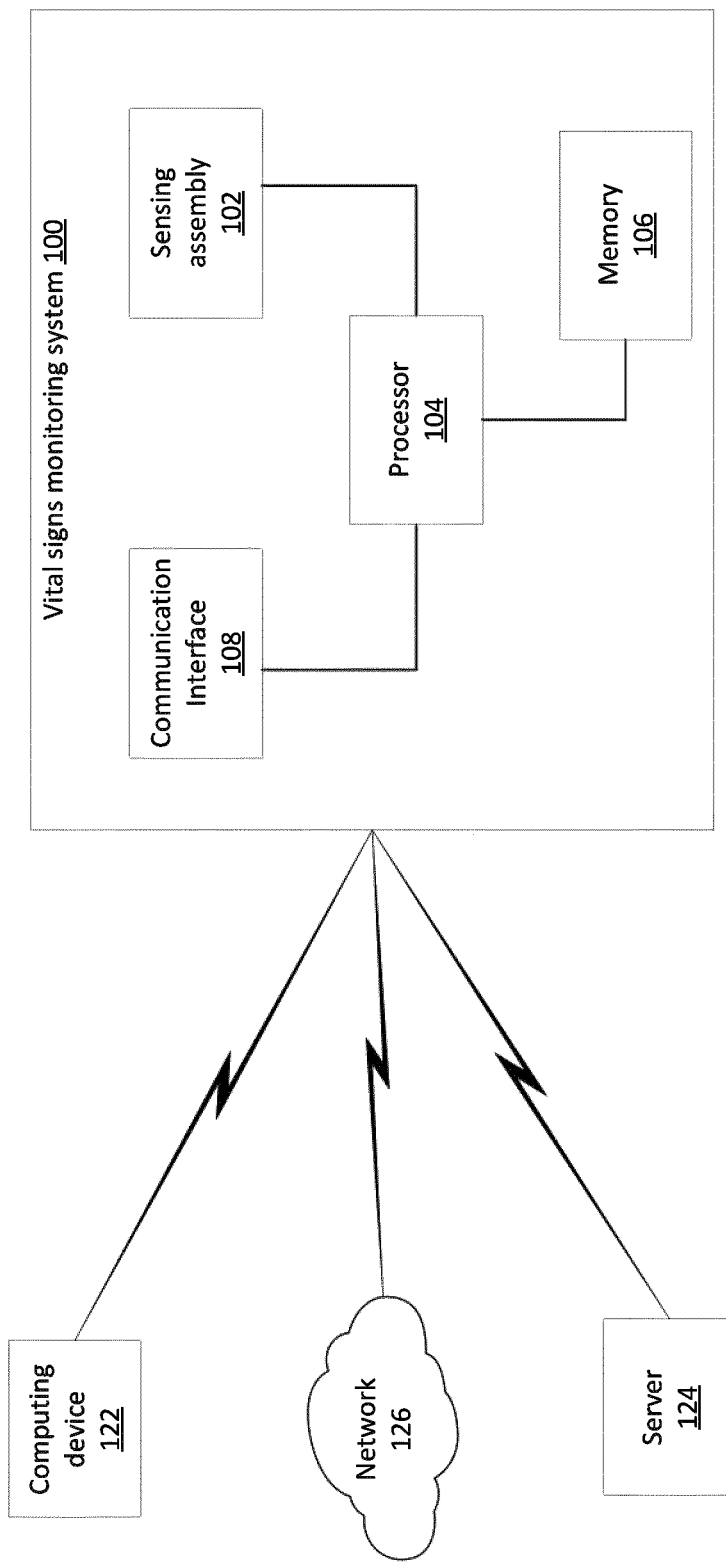
FIG. 1 illustrates a block diagram of a vital signs monitoring system according to an exemplary embodiment of a disclosure.

The following description is presented to enable any person skilled in the art to make and use the described embodiments, and is provided in the context of a particular application and its requirements. Various modifications to the described embodiments will be readily apparent to those skilled in the art, and the general principles defined herein may be applied to other embodiments and applications without departing from the spirit and scope of the described embodiments. Thus, the described embodiments are not limited to the embodiments shown, but are to be accorded the widest scope consistent with the principles and features disclosed herein.

As used herein, the term "electrocardiography (ECG)" refers to t h e changes of the electrical potential due to the depolarization of heart muscle. R-peak of the ECG signal can be used in the calculation of time intervals for monitoring blood pressure (e.g. RJ-time interval), R-peak or Q-peak of ECG signal for monitoring cardiac activity (e.g. pre-ejection period (PEP) and its influencing parameters such as hormones, preload, afterload, etc.) or as the trigger to start data measurement/analysis. The term "seismocardiography (SCG)" refers to the acceleration of the sternum caused by the cardiac activity of the heart while the term "ballistocardiography (BCG)" refers to the changes in the center of mass of the body due to blood flow or heart activity. As used herein, a new term is introduced here. The term "Mass Transit Time (MTT)" refers to the time interval between the start of the blood ejection from the heart to the time where blood turns at the arches of the aorta or any other specific locations where the change in the blood flow can be detected. It is a mass transit time because we are detecting the transit of the mass of blood and the resulting impulse of the mass movement to the torso of the body. The J-peak of the RJ-time interval comes from the peak obtained from either SCG or BCG. In an example case where a tri-axis accelerometer is used for SCG measurement, the J-peak of the SCG is labeled as Jx-peak for acceleration in the X-axis (also referred as head-to-foot axis), Jy-peak for acceleration in the Y-axis (also referred as right-left axis) and $J_z$-peak for acceleration in the Z-axis (also referred as dorso-ventral axis). For simplicity, for use herein, $J_z$-peak can refer to any point on the Z-axis acceleration or as labeled in FIG. 4 as $J_{z1}$-, $J_{z2}$-, or $J_{z3}$-peak as an example, for better or easier peak detection in the algorithm. Accelerometer signal detected on Z-axis (also referred as dorso-ventral axis) measures the chest movement due to heart contraction. $J_z$-peak can be used with ECG signal (e.g. R-$J_z$, or Q-$J_z$ time interval) to investigate important cardiac activity such as the pre-ejection period (PEP) and its influencing parameters such as hormones, preload, afterload, etc. Accelerometer signal (detected on X-axis (also referred as head-to-foot axis) measures the body recoil movement due to blood flow. Jx-peak signifies the time where blood pumps out from the heart and reaches the arches of Aorta blood vessel. One example will be R-Jx time interval for blood pressure monitoring. In the measurement of the time intervals, R-peak of ECG or Jz-peak of accelerometer can be used to trigger the start of measurement.

The blood pressure monitoring can also be performed solely using SCG or accelerometers (e.g. $J_z$-$J_x$ time interval). Again here, $J_z$-peak refers to either $J_{z1}$-peak or $J_{z2}$-peak or $J_{z3}$-peak or any other points along Z-axis, and is used depending on which gives a better or easier detection. For example, $J_{z1}$-peak signifies the time where heart contracts while $J_{z3}$-peak signifies the time where blood starts rushes out of the heart and $J_x$-peak signifies the time where the blood rushes through the arches of the Aorta blood vessel. This time interval is inversely correlated to the blood pressure. $J_z$-peak can also be used as the trigger to start data measurement/analysis. $J_x$-peak can be used in the calculation of time intervals for monitoring blood pressure (e.g. R-Jx time interval, Jz-Jx time interval, or Jx with photoplethysmogram (PPG) signal time interval). The term "photoplethysmography (PPG)" refers to the changes in light adsorption in blood. Depending on the position where the PPG data is taken, the time interval between R-peak with PPG, Jz-peak (from SCG) with PPG, Jx-peak (from SCG) with PPG, PPG in one location with PPG in another location, can be used to monitor blood pressure or blood flow velocity.

FIG. 1 illustrates an exemplary embodiment of a vital signs monitoring system 100. The system 100 can be either removably worn by a target, i.e. a patient, applied to, or placed at a sternum of the target and configured to either continuously, semi-continuously, or synchronously detected at least one signal. In some embodiments, the system 100 can be implanted into the target. In another embodiment, the system 100 can be integrated into a client device either worn by the target, applied to, or positioned placed at the sternum of the target and configured to either continuously, semi-continuously, or synchronously detected at least one signal. As some examples, the client device may be a patch, a neckless, a chest strap, a pendant, or any suitable device. If the system 100 is implantable into the target, the system 100 may be a pacemaker, or any suitable implantable device. The system 100 includes a sensing assembly 102, a processor 104, a memory 106, a communication interface 108, and any suitable computer implemented modules communicatively coupled to each other via a bus. A housing may be provided to encapsulate at least one or more of the sensing assembly 102, the processor 104, the memory 106, and the communication interface 108. In one embodiment, the housing may be formed from a thin film material that allows the target to stretch, bend, twist, squeeze, fold, expand, or combination thereof either worn by the target, applied to, reapplied to, removed from, or positioned placed at the sternum of the target. The memory 106 communicatively coupled to the processor 104 stores computer-readable instructions that, when executed by the processor 104 of the system 100, causes the system, and more particularly the processor 104, to perform or monitor vital signs and cardiac activity based on the detected signal transmitted by the sensing assembly 102. The memory 106 may include any transitory, non-transitory, volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. The vital signs include body temperature, pulse rate, blood pressure, blood speed, and respiratory rate.

The processor 104 may be of any type, including but not limited to a microprocessor, a microcontroller, a digital signal processor, or any combination thereof. The processor 104 may include one or more levels of caching, such as a level cache memory, one or more processor cores, and registers. Depending on the desired configuration, the processor may be of any type, including but not limited to a microprocessor (µP), a microcontroller (µC), a digital signal processor (DSP), or any combination thereof. The processor may include one or more levels of caching, such as a level cache memory, one or more processor cores, and registers. The example processor cores may (each) include an arithmetic logic unit (ALU), a floating point unit (FPU), a digital signal processing core (DSP Core), or any combination thereof. An example memory controller may also be used with the processor, or in some implementations the memory controller may be an internal part of the processor.

The communication interface 108 allows software and data to be transferred between a computer system external to the system 100 and the system in the form of signals which may be, for example, electronic, electromagnetic, optical, or other signals capable of being received by the communication interface. The communication interface may be for example a modem, a network interface, a communication port, a PCM-CIA slot and card, or the like.

The sensing assembly 102 is configured to detect at least one or more of electrocardiogram (ECG) signal, a first motion signal, a second motion signal, a photoplethysmorgram (PPG) signal, seismocardiogram signal (SCG) and ballistocardiogram (BCG) signal. In one embodiment, the sensing assembly 102 is a single-axis sensing assembly. In another embodiment, the sensing assembly 102 is a double-axis sensing assembly. In yet another embodiment, the sensing assembly 102 is a multi-axis assembly. As an example, the sensing assembly 102 includes at least one sensor device. The sensor device may be an accelerometer, a motion sensor, an optical sensor, a transducer, a Doppler ultrasonic transducer, an acoustic sensor, an electrode, an ECG sensor, a target orientation sensor, a sonar sensor, a thermal sensor, an environmental sensor, and any suitable sensor or transducer. As an example, a first sensor device located at a first axis of the target for detecting a first time-dependent motion waveform representative of one or more contractile properties of the target's heart and a second sensor device located at a second axis of the target for detecting a second time dependent motion waveform representative of the target's blood flow. As another example, a multi-axes sensor device located at both first and second axis of the target for detecting a first time-dependent motion waveform representative of one or more contractile properties of the target's heart and for detecting a second time dependent motion waveform representative of the target's blood flow. In some embodiment, the sensing assembly comprises a first sensing axis located at a first axis of a target generating a first time-dependent motion waveform representative of one or more contractile properties of the target's heart and a second sensing axis located at a second axis of the target generating a second time dependent motion waveform representative of the target's blood flow. Additional sensors provided at a location along any axis of the target to either remove motion artifacts (as a reference sensor) or detect attributes from the environment for providing context awareness information.

The system 100 may be a wired computing system or a wireless computing system. In one embodiment, the system 100 is a cloud computing device which may be communicated with via the Internet, and which may be co-located or geographically distributed, wherein shared resources, software, and information are provided to computers and other devices on demand for example, as will be appreciated by those skilled in the art. In another embodiment, the cloud blood pressure system 100 may be implemented as one or more servers which may be communicated with via the Internet. The system 100 may communicatively couple to a computing device 122, a server 124, or a network 126 via one or more links. The link may be wired, wireless, or combination thereof. The wireless communication link may include cellular protocol, data packet protocol, radio frequency protocol, satellite band, infrared channel, or any other protocol able to transmit data among client machines. The wired communication link may include any wired line link.

Depending on the application, one or more servers may be communicatively coupled to the computing device 122 and the system 100. The server 124 may be an application server, a certificate server, a mobile information server, an e-commerce server, a FTP server, a directory server, CMS server, a printer server, a management server, a mail server, a public/private access server, a real-time communication server, a database server, a proxy server, a streaming media server, or the like. The client machine 122 may be a personal computer or desktop computer, a laptop, a cellular or smart phone, a tablet, a personal digital assistant (PDA), a gaming console, an audio device, a video device, an entertainment device such as a television, a vehicle infotainment, a wearable device, a thin client system, a thick client system, or the like. The client machine 122 can in some embodiment be referred to as a single client machine or a single group of client machines, while the server 124 may be referred to as a single server or a single group of servers. In one embodiment a single client machine communicates with more than one server, while in another embodiment a single server communicates with more than one client machine. In yet another embodiment, a single client machine communicates with a single server.

The network 126 can comprise one or more sub-networks, and can be installed between any combination of the client machines 122 and the server 124. In some embodiments, the network 126 can be for example a local-area network (LAN), a metropolitan area network (MAN), a wide area network (WAN), a primary network 126 comprised of multiple sub-networks located between the client machines 122 and the server 124. Still further embodiments include the network 126 that can be any network types such as a point to point network, a broadcast network, a telecommunication network, a data communication network, a computer network, an ATM (Asynchronous Transfer Mode) network, a SONET (Synchronous Optical Network) network, a SDH (Synchronous Digital Hierarchy) network, a wireless network, a wireline network, and the like. Depending on the application, other networks may be used so that data exchanged between the client machine and the server can be transmitted over the network. Network topology of the network 124 can differ within different embodiments which may include a bus network topology, a star network topology, a ring network topology, a repeater-based network topology, or a tiered-star network topology. Additional embodiments may include a network of mobile telephone networks that use a protocol to communicate among mobile devices, where the protocol can be for example AMPS, TDMA, CDMA, GSM, GPRS, UMTS, LTE or any other protocol able to transmit data among mobile devices.

Figure 2:
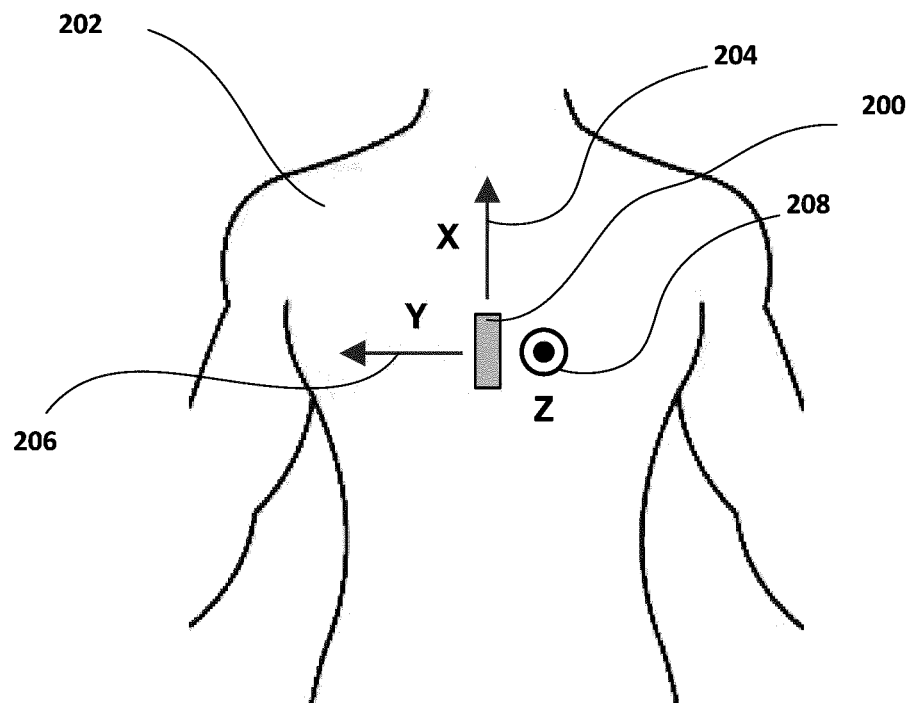
FIG. 2 illustrates a target with a vital signs monitoring system of FIG. 1 placed on a sternum of the target according to a described embodiment of the disclosure.

FIG. 2 illustrates a target 202, such as a user or a patient, with a vital signs monitoring system 200 according to a described embodiment of the disclosure. The system 200 identical to the system 100 depicted in FIG. 1 is placed on a sternum of the target and configured to continuously, semi-continuously, or synchronously detect or monitor at least one or more of electrocardiogram (ECG) signal, a first motion signal, a second motion signal, a photoplethysmorgram (PPG) signal, a seismocardiogram (SCG) signal, a ballistocardiogram (BCG) signal or environmental signal. In some embodiments, the system 200 is placed on the sternum of the target for sensing movement of the chest wall. Since bones can transfer the body movement due to cardiac activities with less damping effects than muscles, the system 200 is able to detect the signal that is less affected by motion artifacts. In another embodiment, the system 100 may be placed on any location of the body proximal to the sternum of the target. In yet another embodiment, the system 200 is configured to detect the time interval between heart contraction and blood flow.

As illustrated, X-axis 204, Y-axis 206, and Z-axis 208 are provided. A first sensor device of the system 100 located at a first axis of the target for continuously detecting a first time-dependent motion waveform representative of one or more contractile properties of the target's heart and a second sensor device located at a second axis of the target for continuously detecting a second time dependent motion waveform representative of the target's blood flow. The first axis is the dorso-ventral axis and the second axis is the head-to-foot axis. The axis can be interchangeable between x, y, and z depending on position arrangement of the system 200. If the system 200 is pointing at X-axis 204, as illustrated in FIG. 2 the first axis is the Z-axis 208 and the second axis is the X-axis 204. In another embodiment, the system 200 is pointing at Y-axis 206, the first axis is the Z-axis 208 and the second axis is the Y-axis 206.

The sensor devices may be a single-axis sensor device or a double-axis sensor device. In another embodiment, the sensor device is a multi-axis sensor device configured to map the resulting vector along the axis of interest, e.g. if the multi-axis sensor device is rotated and not completely aligned with for example the head-to-foot axis. As illustrated, the first and second sensor devices are accelerometers. In another embodiments, a multi-axes can be placed on both the first, second and third axis of the target. At the first axis, a first time-dependent motion waveform representative of one or more contractile properties of the target's heart is generated. At the second axis, a second time-dependent motion waveform representative of the target's blood flow is generated. And at the third axis, the data is used to map the resulting vector of axis of interest, e.g. if the sensor is rotated and not completely aligned with for example the head-to-foot axis.

Figure 3:
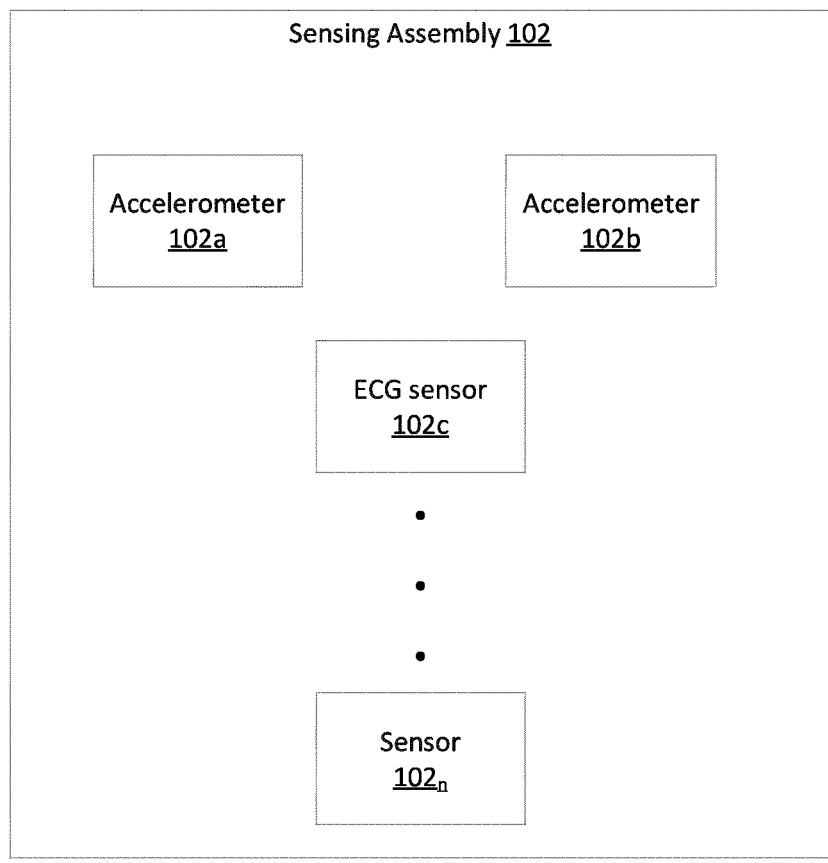
FIG. 3 illustrates a sensing assembly for the vital signs monitoring system of FIG. 1 according to a described embodiment of the disclosure.

FIG. 3 illustrates a sensing assembly 102 for the blood pressure monitoring system 100. The sensing assembly 102 is configured to detect at least one or more of electrocardiogram (ECG) signal, a first motion signal, a second motion signal, a photoplethysmorgram (PPG) signal, seismocardiogram (SCG) signal and ballistocardiogram (BCG) signal. In one embodiment, the sensing assembly 102 is a single-axis sensing assembly. In another embodiment, the sensing assembly 102 is a double-axis sensing assembly. In yet another embodiment, the sensing assembly 102 is a multi-axis assembly. As an example, the sensing assembly 102 includes at least one sensor device. The sensor device may be an accelerometer, a motion sensor, an optical sensor, a transducer, a Doppler ultrasonic transducer, an acoustic sensor, an electrode, an ECG sensor, a target orientation sensor, a sonar sensor, a thermal sensor, an environmental sensor, and any suitable sensor or transducer. As an example, a first sensor device located at a first axis of the target generates a first time-dependent motion waveform representative of one or more contractile properties of the target's heart and a second sensor device located at a second axis of the target generates a second time dependent motion waveform representative of the target's blood flow. As another example, a third sensor device located at any axis of the target generates a third time dependent waveform representative of the electrical potential due to the depolarization of heart muscle. In one embodiment, the first and second sensor devices are accelerometers 102a, 102b and the third sensor device 102c is either an electrode or an ECG sensor. In another embodiment, a fourth sensor located along any axis of the target is provided and is configured to either detect attributes from the environment for providing context awareness information or remove motion artifacts (as reference sensor). In another embodiment, the first sensor and second sensor is integrated into a multi-axes sensor (102a and 102b integrated in a multi-axes sensor).

Figure 4:
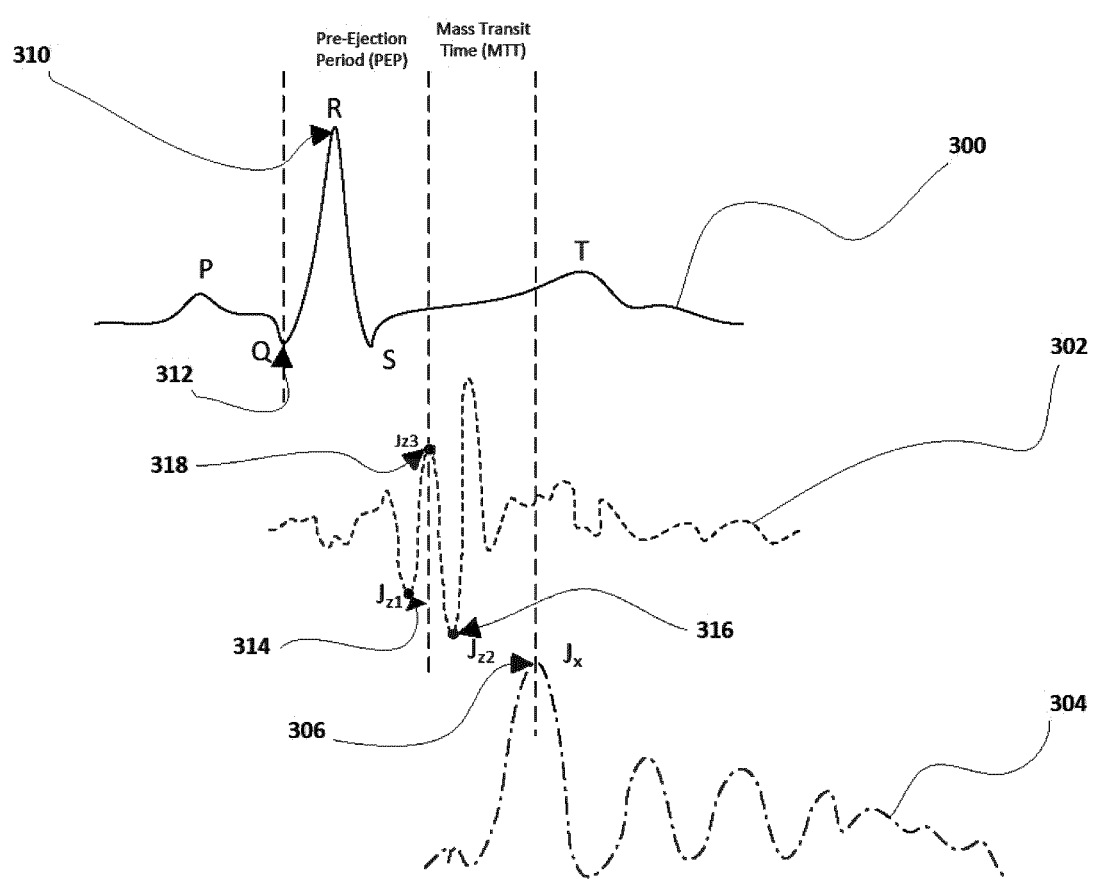
FIG. 4 illustrates a graph of time-dependent waveforms according to an exemplary embodiment of the disclosure.

FIG. 4 illustrates time-dependent waveforms, ECG waveform 300, a first motion waveform 302, and a second motion waveform 304 continuously monitored by the blood pressure system to determine the target's vital sign, i.e. blood pressure and cardiac activity (e.g. PEP and its influencing parameters). The ECG waveform 300, generated by the ECG sensor 102c of the sensing assembly 102 placed on the target represents the electrical excitation of the heart, features a peak 310. The first motion waveform 302 generated by the first accelerometer 102a of the sensing assembly 102 represents the chest movement due to the heart contraction or the cardiac activity of the heart.

In one embodiment, the first motion waveform 302 is a SCG waveform in the Z-axis. In another embodiment, the first motion waveform 302 is a BCG waveform in the Z-axis. The second motion waveform 304, generated by the second accelerometer 102b of the sensing assembly 102 represents the body recoil movement due to the blood flow, features a peak 306. In one embodiment, the second motion waveform 304 is a SCG waveform in the X-axis. In another embodiment, the second motion waveform 304 is a BCG waveform in the X-axis. In another embodiment, the first motion waveform 302 and the second motion waveform 304 is generated by a multi-axes sensor (e.g. an accelerometer) located at both the first and second axis of the target. In another embodiment, one multi-axes sensor is used at each axis (first and second or third), to generate a combined data of all three axes (X, Y, Z) for better performance.

The peak 310 also referred as R-peak of ECG waveform 300 may be used either in the calculation of time intervals for monitoring blood pressure, vital signs and cardiac activity or to trigger a start of blood pressure measurement. The peak 312 also referred as Q-peak of ECG waveform 300 may also be used in the calculation of time intervals for monitoring blood pressure, vital signs and cardiac activity or to trigger a start of blood pressure measurement. Any points along the first motion waveform 302 may be used in calculation of time intervals for monitoring blood pressure, vital signs and cardiac activity or to trigger a start of blood pressure measurement. As an example, the peak 314 may be used in calculation of time intervals for monitoring blood pressure, vital signs and cardiac activity or to trigger a start of blood pressure measurement. As another example, the peak 316 may be used in calculation of time intervals for monitoring blood pressure, vital signs and cardiac activity or to trigger a start of blood pressure measurement. As another example, the peak 318 may be used in calculation of time intervals for monitoring blood pressure, vital signs and cardiac activity or to trigger a start of blood pressure measurement.

Any points along second motion waveform 304 may be used in the calculation of time intervals for monitoring blood pressure, vital signs and cardiac activity. As one example, the peak 306 may be used in the calculation of time intervals for monitoring blood pressure, vital signs and cardiac activity. In one embodiment, the time difference between the peaks 306, 310 is the combination of the pre-ejection period (PEP) plus the mass transit time (MTT). In another embodiment, the time difference between any points 312 located along the ECG waveform 300 and the peak 306 of the second motion waveform 304 features the PEP+MTT time interval. As an example, the point 312 is located at Q.

As described previously, pre-ejection period (PEP) is defined between two points located along waveforms 300, 302. In one embodiment, $J_{z1}$-peak 314 located along the waveform 302 can be used with point Q 312 along the ECG waveform 300 to investigate important cardiac activity such as the pre-ejection period (PEP) and its influencing parameters such as hormones, preload, afterload, etc. In yet another embodiment, $J_{z2}$-peak 316 located along the waveform 302 can be used with point Q 312 along the ECG waveform 300 to investigate important cardiac activity such as the pre-ejection period (PEP) and its influencing parameters such as hormones, preload, afterload, etc. In yet another embodiment, $J_{z3}$-peak 318 located along the waveform 302 can be used with point Q 312 along the ECG waveform 300 to investigate important cardiac activity such as the pre-ejection period (PEP) and its influencing parameters such as hormones, preload, afterload, etc. In yet another embodiment, $J_{z1}$-peak 314 located along the waveform 302 can be used with peak R 310 along the ECG waveform 300 to investigate important cardiac activity such as the pre-ejection period (PEP) and its influencing parameters such as hormones, preload, afterload, etc. In further yet another embodiment, $J_{z2}$-peak 316 located along the waveform 302 can be used with peak R 310 along the ECG waveform 300 to investigate important cardiac activity such as the pre-ejection period (PEP) and its influencing parameters such as hormones, preload, afterload, etc. In further yet another embodiment, $J_{z3}$-peak 318 located along the waveform 302 can be used with peak R 310 along the ECG waveform 300 to investigate important cardiac activity such as the pre-ejection period (PEP) and its influencing parameters such as hormones, preload, afterload, etc. As one embodiment, the time difference between $J_{z1}$-peak 314 of the waveform 302 and the peak 306 of the waveform 304 features the mass transit time (MTT). As another embodiment, the time difference between $J_{z2}$-peak 316 of the waveform 302 and the peak 306 of the waveform 304 features the mass transit time (MTT). In yet another embodiment, the time difference between $J_{z3}$-peak 318 of the waveform 302 and the peak 306 of the waveform 304 features the mass transit time (MTT).

The time interval between the $J_z$-peak of the dorso-ventral axis to the $J_x$-peak of the head-to-foot axis signifies the time it takes for the heart to start contracting till the time the blood flow reaches the arches of the aorta. This $J_z$-$J_x$ time interval can be used to monitor blood pressure or relative blood pressure. The time interval can also be used to monitor other cardiovascular parameters such as arterial stiffness, as one example or cardiac output as another example.

As described above, blood pressure can be monitored by measuring the blood flow velocity profile of two PPG signals at two different locations at the time intervals. Alternatively, the blood flow velocity can be measured using a Doppler ultrasonic transducer. This method uses reflection of ultrasonic irradiation of frequency f0 from the blood in any arteries, e.g. the Aorta, with additional ultrasonic frequencies appearing in the reflected wave spectrum as sidebands at spectral position f0+/−Δf, with Δf being a time-dependent function of blood velocity v(t):

$$\Delta f(t) = \Delta f(v) = \Delta f(v(t)) \qquad \text{equation (1)}$$

The minimum reading of Δf in between 2 maxima ΔfA, namely Δfmin has a correlation to the minimum blood velocity vmin and to blood pressure as well. The term Δfmin or vmin corresponds to the diastolic blood pressure.

The measurement of Δf can be done by synchronous demodulation of the reflected ultrasonic signal spectrum with the center frequency f0 into the base-band, by a combination of mixing stage and low-pass filter, or any suitable FM-demodulation technique. Phase-locked loop demodulators, ratio-detectors, and any suitable active components, depending on the applications, may be used.

In yet another embodiment, the sensor device may be any suitable piezoelectric or electrostatic/capacitive bending actuator or bimorph configured to convert an electrical carrier frequency signal at f0 into an ultrasonic wave, and an incoming ultrasonic wave spectrum is converted back to an electrical signal spectrum for further analysis. In addition, at least one accelerometer signal can be used, depending on the application, to trigger the ultrasonic irradiation and evaluation loop, for cross-correlating data, and for providing context-awareness information. More than one accelerometer of the system 200 can also be used to detect if the user is moving or the kind of activity the user is doing, to add additional information to the user. The additional accelerometer can also be utilized to reduce/filter motion artifacts from the Jx or Jz data.

Figure 5:
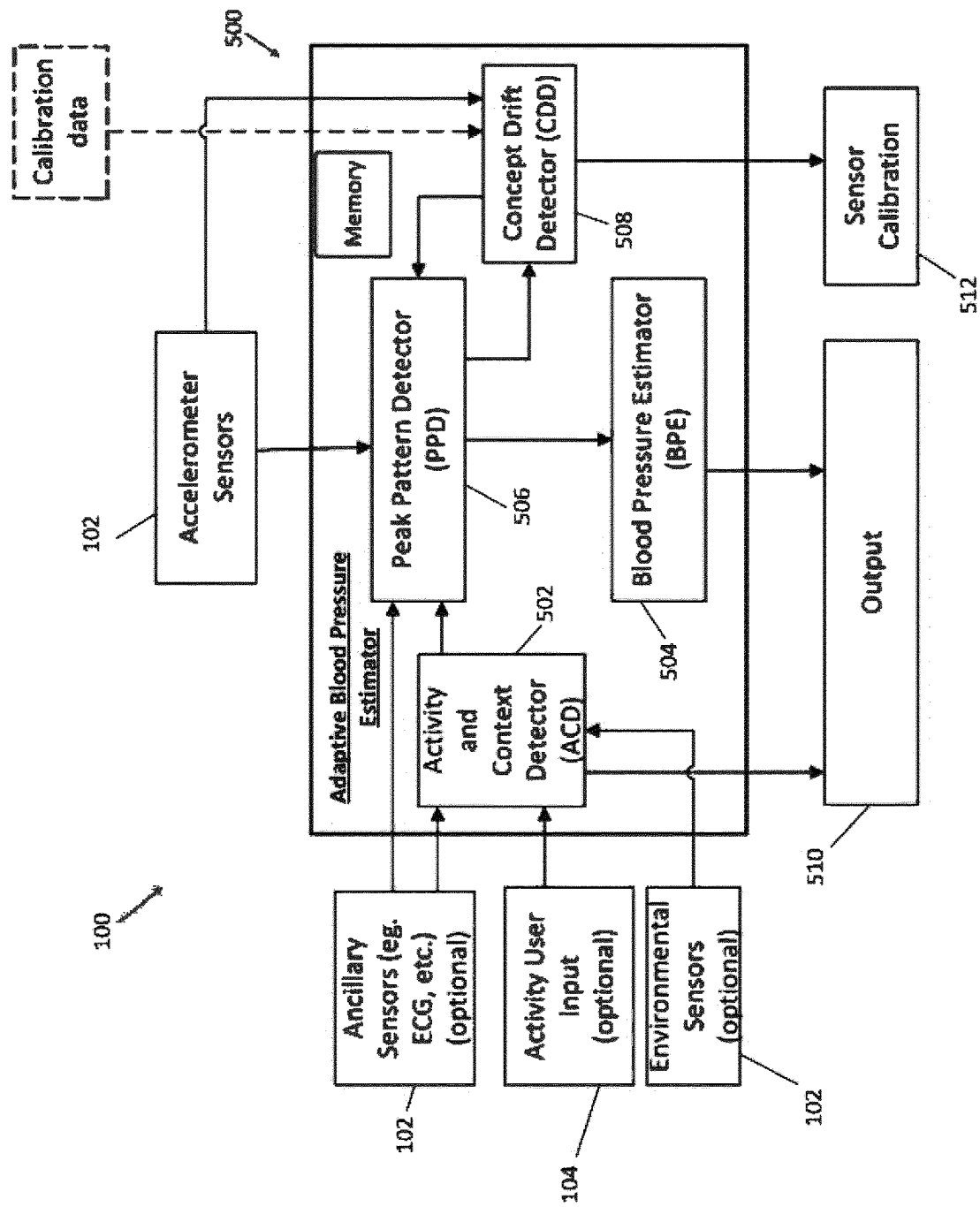
FIG. 5 illustrates a simplified block diagram of a vital signs monitoring system in accordance to another alternative embodiment of the disclosure.

FIG. 5 illustrates a simplified block diagram of a vital signs monitoring system 100 according to an exemplary embodiment of a disclosure. The system 100 comprises one or more sensors 102, a user interface 104, and an adaptive blood pressure estimating control system 500.

The sensors 102 configured to collect raw data comprises accelerometer sensors, ancillary sensors, environmental sensors, or any sensors suitable for the system. In one embodiment, the accelerometer sensor may be single axis or multi-axes accelerometer measures the acceleration in at least two axes. In some embodiment, sensors such as ancillary sensors or environmental sensors for detecting vital signs and environmental measurements may be used. The system is placed on the subject's chest as shown previously. In one example, the output of the sensors is the primary source of raw data used by the system. Additional data that may be used by the statistical model as input, may be obtained from other sensors including and not limited to motion sensors, optical sensors, acoustic sensors, transducers, Electrocardiogram (ECG) sensors, orientation and global positioning sensors, sonar sensors, thermal sensors, environmental sensor, etc. External data sources like e.g. weather data can also be used to improve the model. In addition, calibration data can be included to calibrate the blood pressure value.

Data from the accelerometers placed on the patient's chest, for example, implicitly or explicitly capture a time-dependent motion waveform representation of the subject's blood flow, and contractile properties of the target heart. The feature extraction component of the framework does the necessary data transformations to obtain data features that may be used to model the estimated blood pressure measurements. In order to be able to extract relevant features from noise in the data, pre-processing of the raw features is needed. The pre-processing functionality removes ambient noise, linear trends, drifts, outliers, motion artifacts, etc. in the raw data before the framework can extract rich features that are to be fed as input to the blood pressure estimation model. Frequency domain filtering using high/low/band filters, anomaly detection, normalization, sliding window and trend and drift compensation are few of the popular approaches used to remove noise.

The control system includes a processor (104, FIG. 1) and memory 106. Software and/or hardware components of the control system 106 are configured to implement a pre-processing model (that extracts features from raw data), a statistical model (returns real time blood pressure measurements as output), a post processing model (integrates context awareness and concept adaptability to the statistical model results) and an output component that presents the results from the models in a relevant format that is of interest to the subject being monitored.

The statistical model is an adaptive, user-specific, data-driven model for monitoring blood pressure measurements that takes in streaming data as input and returns real-time results of the blood pressure estimated. The statistical model for blood pressure monitoring can be executed solely using data from accelerometers that capture when the heart contracts and when the blood rushes through the arches of the Aorta blood vessel, since this time interval is inversely correlated to the blood pressure. Hence features from the accelerometer are valuable and used by the framework. Data from sensors detecting vital signs (such as contractile properties of the subject's heart and blood flow), and sensor that capture environmental measurements such as temperature, humidity, pressure, motion, and sea level elevation, are used to enhance the predictive strength of the statistical models and make it more robust and invariant to noise in the collected raw data. The statistical model is not limited to blood pressure monitoring. It can include other functionalities such as cardiac output or cardiac health, and other health and wellness related parameters.

A few of the input data features capturing the following information are known to have higher predictive power for the statistical model including changes of the electrical potential due to the depolarization of heart muscle (ECG signal), changes in the center of mass of the body due to blood flow or heart activity (Ballistocardiogram (BCG), acceleration of the sternum or other parts of the body caused by the cardiac activity of the heart (Seismocardiogram (SCG), and motion of the body due to respiration (SCG).

The statistical model implemented by the control system may perform peak-detection, blood pressure prediction modeling, context awareness, and concept drift detection and adaptability.

Figure 6:
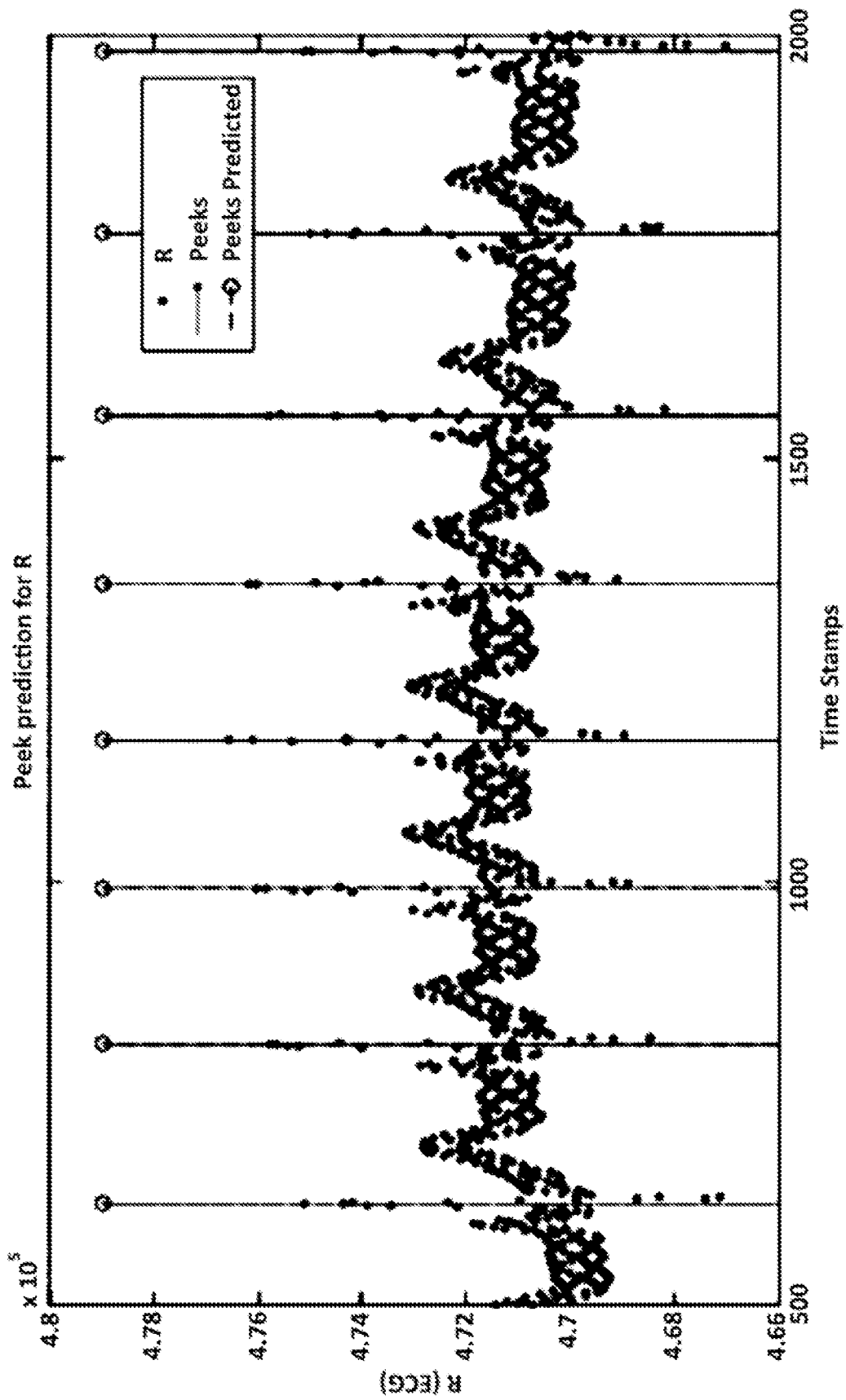
FIG. 6 illustrates a simplified graph according to a described embodiment of the disclosure.
Figure 7:
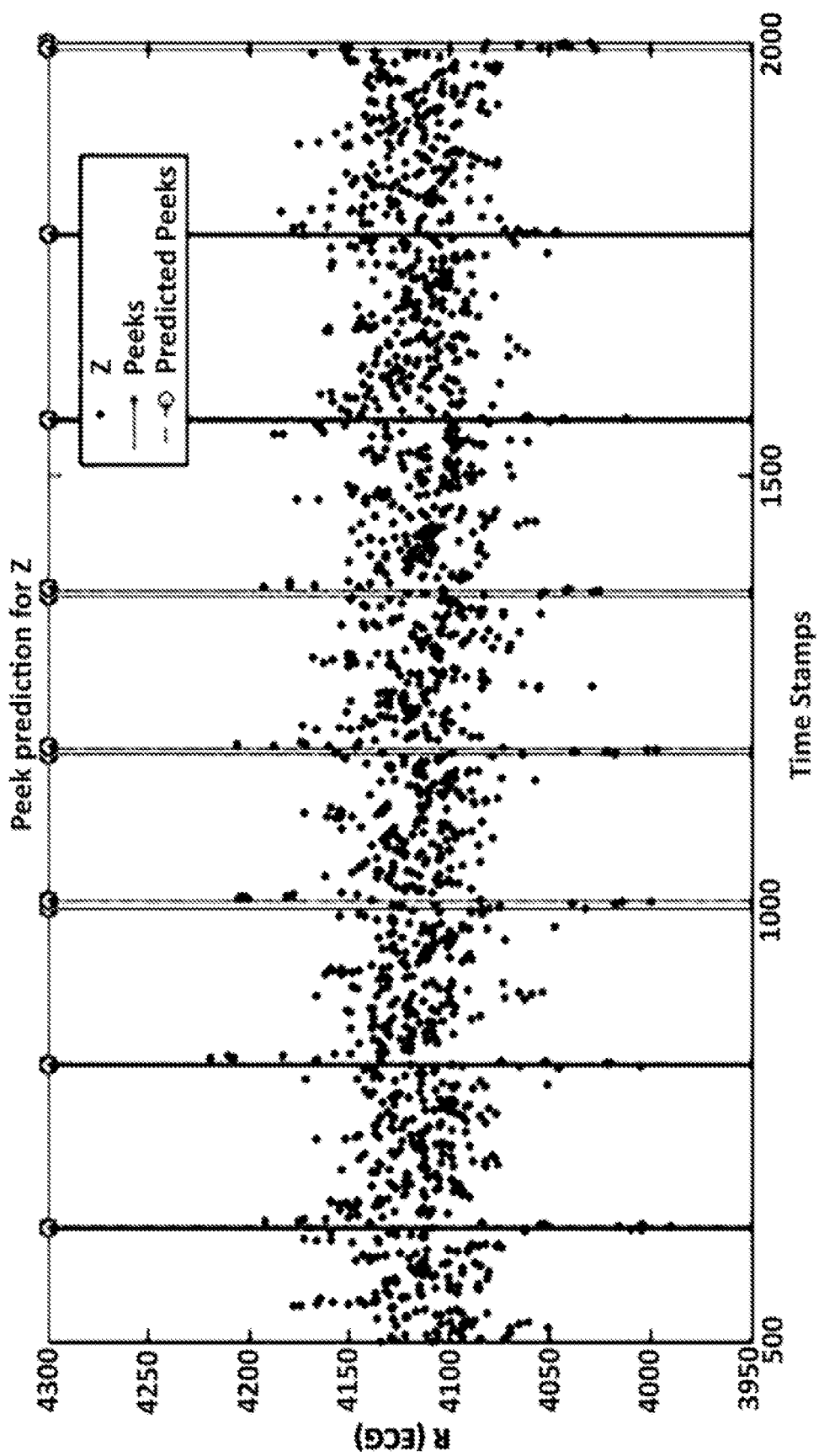
FIG. 7 illustrates a simplified graph according to a described embodiment of the disclosure.
Figure 8:
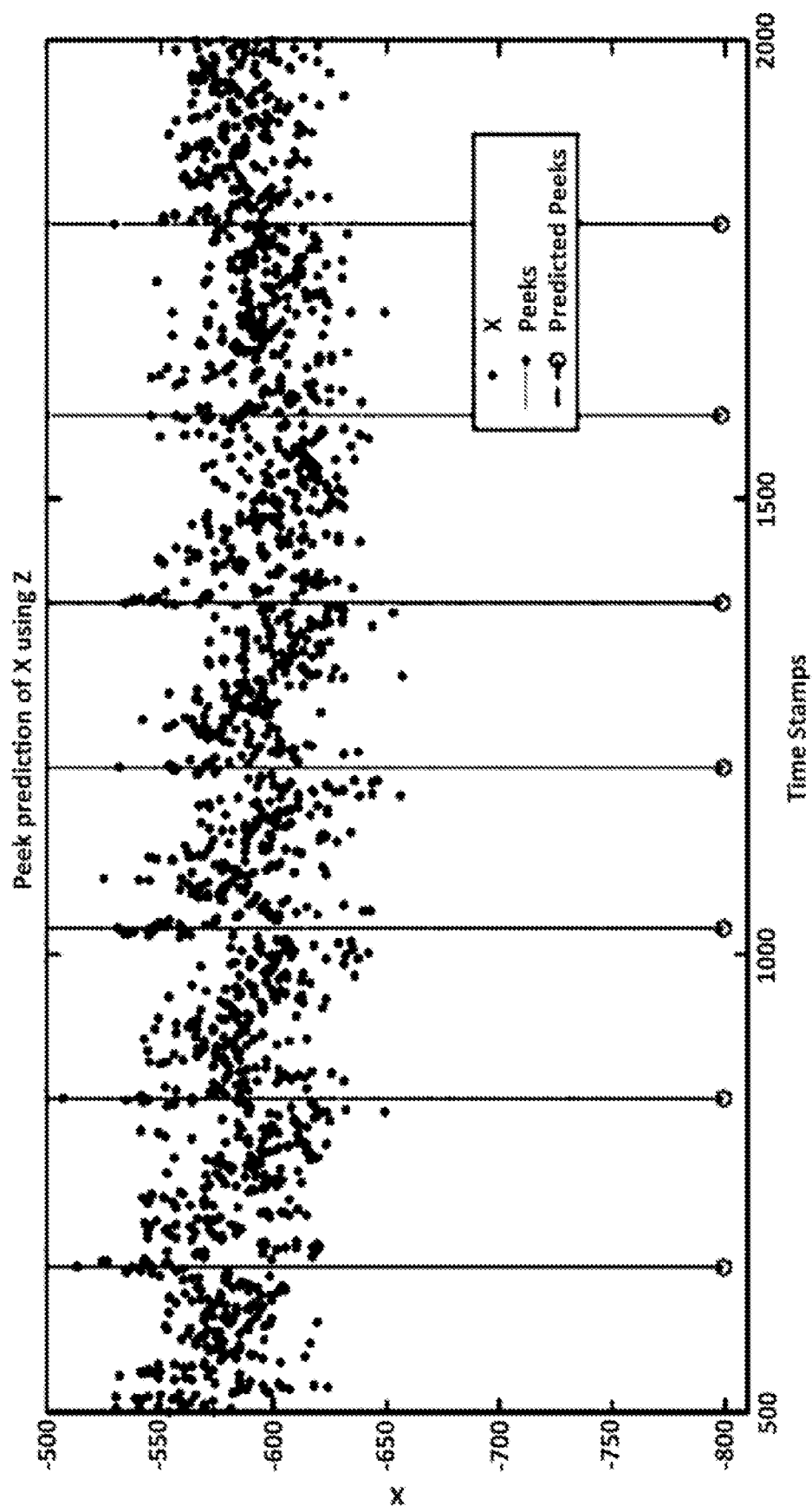
FIG. 8 illustrates a simplified graph according to a described embodiment of the disclosure.

The peak detection functionality of the statistical model identifies relevant peaks in the ECG, BCG and SCG signal that can be used to identify the exact timestamp when the heart contracts and when the blood rushes through the arches of the Aorta blood vessel. This information is then used from the blood pressure prediction model to estimate the blood pressure. ECG peak detection can be optionally used depending on the use cases, e.g. as trigger for SCG detection. For the purpose of the rest of this document, peaks of interest obtained from either SCG or BCG are referred to as J-peaks. Three of the important types of peaks within the time dependent motion waveform representing SCG and BCG are: $J_x$-peak for acceleration in the X-axis (also referred as head-to-foot axis), $J_y$-peak for acceleration in the Y-axis (also referred as right-left axis), and $J_z$-peak for acceleration in the Z-axis (also referred as dorso-ventral axis). $J_z$-peak signifies the time where heart contracts. It can also be used along with ECG signal to investigate important cardiac activity such as the pre-ejection period (PEP) and its influencing parameters such as hormones, preload, afterload, etc. $J_x$-peak signifies the time where blood pumps out from the heart and reaches the arches of Aorta blood vessel. $J_z$-peak of accelerometer can also be used to trigger the start of measurement. Few of the more informative features used by the peak detection model to identify peaks of importance in the BCG, ECG and SCG signals includes raw values, derivatives, slopes, rate of change in signal amplitude, motifs, moving-average features, distance to various peaks in the signal, and so forth. Linear and non-linear classification models such as logistic regression, support vector machines (SVM), classification and regression trees (CART), neural networks, etc., use the above features as input to predict the peaks. FIG. 6 depicts an example of a graph showing the peaks in an ECG signal and the corresponding predicted peaks. FIG. 7 is an example graph showing the peak prediction for the z-axis from an ECG signal. FIG. 8 is an example graph showing the peak prediction for the x-axis using the z-axis data.

Blood pressure prediction of the statistical model takes as input the time stamps identifying the various peaks in the raw time series signals to compute the blood pressure. The intuition used by the model is that the time interval (from when the heart contracts and the time where the blood rushes through the arches of the Aorta blood vessel,) is inversely correlated to the blood pressure. A linear or non-linear regression model such as contour regression, can be used to model this functionality.

The context awareness functionality of the data driven model enables continued accurate blood pressure monitoring by identifying the impact of change in the ambient environment conditions and changes in activity of the subject on the time-dependent motion waveform being captured. The context awareness functionality integrated heterogeneous data sources from environmental sensors, sensors monitoring the subject to detect in real time changes in user activity and also external data. Changes may often necessitate the need to use different peak detection algorithms or parameters for continuous and accurate monitoring of blood pressure given various types of patterns in the time-dependent motion waveform being captured.

To overcome the need to recalibrate the data driven model to account for changes in the life style of the subject being monitored, a concept drift detection and adaption functionality is incorporated. Concept drift refers to the relationship between the independent input variable and the response variable being modeled. The concept drift detection functionality enables the data-driven model to maintain relevance by tracking changes in the concept being modeled. This is important in a streaming framework that is prone to experience concept drifts. In this application, concept drift is likely to be observed when the subject being monitored changes lifestyle abruptly or gradually over time. Beside lifestyle changes, aging effects of the sensor can also be compensated. This can be done at fixed timing intervals, based on known aging data of the sensor or if e.g. the detection accuracy decreases.

Hypothesis-testing based approaches that track changes in the distribution of input and output data streams and model parameters are used to identify the occurrence of a concept drift. Detection of concept drift is used to inform the subject being monitored of the impact of the change in life style on subject's blood pressure and the cardiac system. Concept drift detection and adaptation approaches, such as Hierarchical Linear Four Rates (HLFR) that uses adaptive SVM in the framework, can be used to dynamically adapt the data driven model to continue to give accurate blood pressure measurements without requiring explicit recalibration when there are changes in lifestyle or characteristics of the subject being monitored. The i/o interface presents the results from the models in a relevant format that is of interest to the subject. The output can include relevant BP values or other health values, context awareness values, calibration values, etc.

In the system 500 of FIG. 5, the activity and context detection, blood pressure estimating, peak pattern detecting, and concept drift detecting functionalities are implemented as modules. As depicted in FIG. 5, the statistical model implemented by the control system includes an activity and context detector (ACD) module 502, blood pressure estimator (BPE) module 504, a peak pattern detector (PPD) module 506, and a concept drift detector (CDD) module 508.

The PPD Module is a multivariate temporal peek pattern detector. An algorithm which is implemented in the PPD Module is depicted in FIG. 11. The PPD Module detects x and z peaks using accelerometer readings as its input. The peaks of z and x detected correspond to peaks in signal z and x, which are used by module BPE to estimate the mass transit time (MTT). The PPD module is a deterministic model that is a function of the probability vector ($\rho(x)$ and $(z)$), that is generated from the accelerometer signal x and z respectively. The element of $\rho(x)$ and $\rho(z)$ corresponding to a score vector that is computed using the preceding 'i' lag measurements from the accelerometer sensor to detect peaks of interest. The score vector captures the probability of the given instance of the accelerometer signal being the local and global peak whether it's a min or max peak, distance to reference and adjacent peaks in x and z, and derivate of the gradient of the peak across an 'i' lag window.

The value of 'i' is dependent on the sample rate (SR) of the accelerometer signal and the expected value of the users heart rate ($\widehat{HR}$), such that $$\frac{\widehat{HR} * SR}{60} > i > \frac{\widehat{HR} * SR}{2 * 60}.$$

The PPD Module detects a peak pattern of interest in signal x at instant 't', when the probability $P(\rho_{t-\Delta}(z)) \geq \tau$, and the probability $P(\rho_t(x)) > \tau$, such that $$\Delta \sim \frac{\widehat{HR} * SR}{60 * \delta}.$$

The constraint ensures that the pattern of interest in z precedes and is approximately $$\frac{\widehat{HR} * SR}{60 * \delta}$$

distance from the occurrence of the peak pattern of interest in signal z. $\delta$ is >2 and represents the expected frequency of the mass transit time (MTT).

The computation of the probability is learned offline and is saved as a model in the PPD module. The bivariate output stream of the PPD module (f(z,x)) are sent to the blood pressure estimator module (BPE) and the concept drift detector module (CDD). In addition to the accelerometer, the PPD module may optionally also receive signals from the activity and context detector module (ACD), concept drift detector module (CDD), ancillary environmental sensor signals and an input channel to modify weights and constants representing the model in the PPD. Input from the ACD module, signals a change in activity or environmental factors affecting the user. A significant change would necessitate using different settings of the model in the PPD module for continued optimal detection of the peak patterns of interest in the z and x signal.

Figure 9:
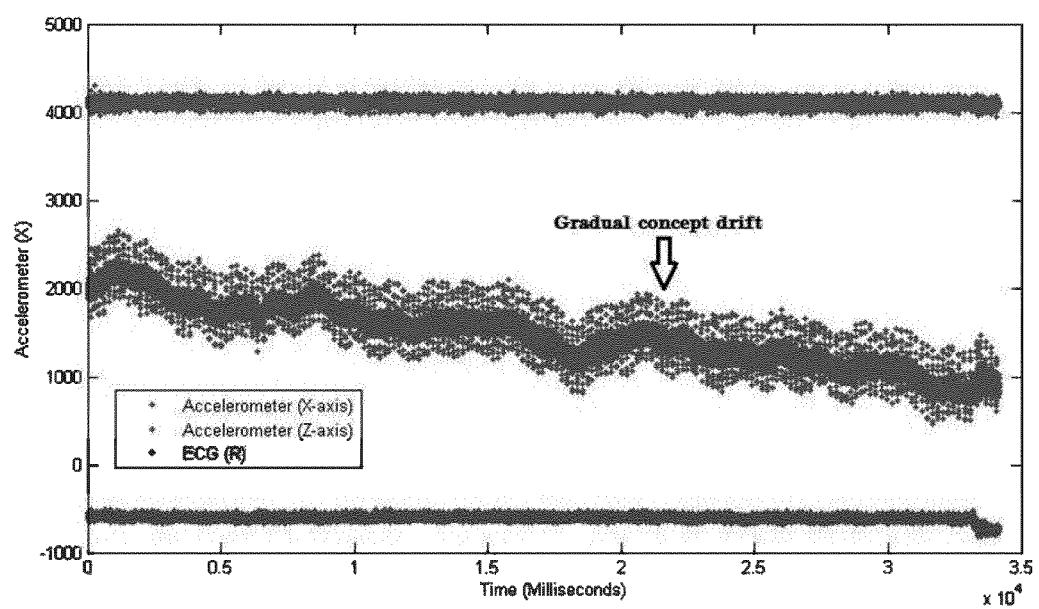
FIG. 9 illustrates a simplified graph according to a described embodiment of the disclosure.

The CDD Module is a concept-drift detector that detects changes in the probability density functions p(z), p(x), the joint probability P(z,x) of the accelerometer z and x signal and distribution of the output from PPD P(f(z,x)). The idea is the changes in joint probability $P(f_z(z,x),z)$, $P(f_x(z,x),x)$ or P(f(z,x)) would signal a change in concept describing the relationship between z and x. Test statistics are used to monitor the error rate of the joint distributions. The purpose of the CDD module is let the blood pressure estimator know if there has been change to the position/contact/efficiency/performance of the accelerometer sensors and other input sensor that may result in deviation of the measurements returned by these sensors. For instance, due to gradual repositioning of degradation of the sensors, there may be gradual drift in measurements in FIG. 9.

An embodiment of an algorithm implemented in the CDD Module is depicted in FIG. 12. The underlying concept for CDD strategy is straightforward: under a stable concept (i.e., $\rho(X_t, y_t)$ remains unchanged), and the corresponding four rate of the confusion matrix (true positive rate (TPR), true negative rate (TNR), false positive rate (FPR) and false negative rate (FNR) $\{P_{TPR}, P_{TNR}, P_{PPV}, P_{NPV}\}$ remains the same over time. Thus, a significant change of any $P_*(* \in \{TPR, TNR, PPV, NPV\})$, implies a change in underlying joint distribution $P(X_t, y_t)$, or concept. More specifically, at each time instant t, LFR conducts statistical tests with the following null and alternative hypothesis:

$$H_0: \forall *, P(\hat{P}_*^{(t-1)}) = P(\hat{P}_*^{(t)})$$

$$H_A: \forall *, P(\hat{P}_*^{(t-1)}) \neq P(\hat{P}_*^{(t)})$$

$$* \in \{TPR, TNR, PPV, NPV\}$$

The concept is stable under $H_0$ and is considered to have potential drift if $H_A$ holds.

The four rates $\{P_{TPR}, P_{TNR}, P_{PPV}, P_{NPV}\}$ are computed in any suitable manner. As one example, ancillary sensors signals such as ECG can be used as the reference variable (Y). Also, the test statistics can be monitored with respect to $\hat{y} \leftarrow f(X, \hat{w})$ learned from the historical data. For the test statistics monitored with respect to $\hat{y_1} \leftarrow f_1(X, \hat{w})$ and $\hat{y_2} \leftarrow f_2(X, \hat{w})$, $f_1$, $f_2$ are orthogonal models learned on the same X. The orthogonal models can be learned in disjoint orthogonal space of the labeled data. This solution doesn't require ground truth or a pseudo equivalent to track errors in the prediction. The orthogonal models are created using the first two orthogonal vectors of the feature space (X) obtained from principal component analysis (PCA).

Figure 10:
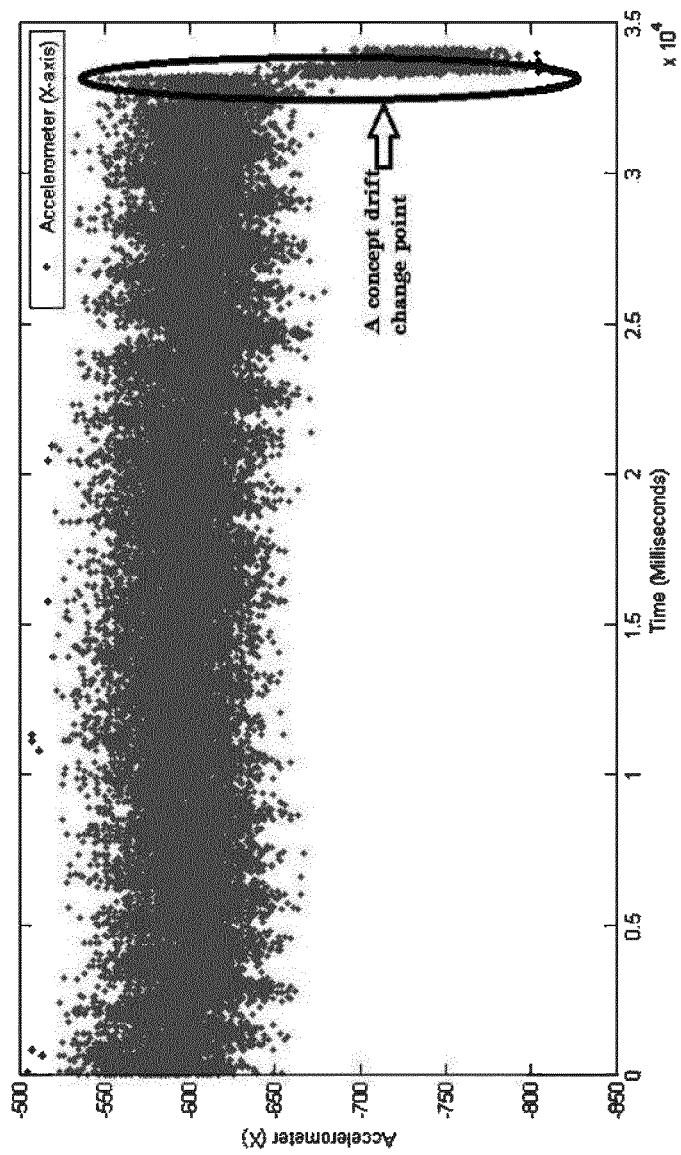
FIG. 10 illustrates a simplified graph according to a described embodiment of the disclosure.

Change points in the input signal that aid in detection of concept drift, such as depicted in FIG. 10, can be naively detected by tracking the change in correlation of features ($\rho(X)$) and change in distribution characteristics of features ($f_z(z,x),z$), $P(f_x(z,x),x)$ or P(f(z,x)). The CDD module provides a feedback to the PPD module to updates the weights of the peek prediction model based on the changes in the concept drift. This updates is incremental in nature. The CDD module also may optionally receive updates regarding calibration that may be used to trigger updating the weights of the PPD module.

The ACD Module is an activity or environmental context change detector. The purpose of the module is to detect posture of the user (lying on the left, lying on the right, lying on the back, sitting, standing, etc.) or activity changes in the user (running, elliptical, jogging, etc) or significant environmental changes that would potentially affect the performance of the PPD module. The module can either be updated either by manual inputs provided by the user or by detecting changes in the concept of the environment/ancillary sensors. Detecting these changes is implemented similar to the CDD module. An embodiment of an algorithm which may be implemented in the ACD Module is depicted in FIG. 13.

An algorithm that may be implemented in the BPE Modules is depicted in FIG. 14. The BPE Module is the blood pressure estimator module that takes as input the identified peak patterns in the z and x signal to estimate the blood pressure of the user as well as the corresponding stats and confidence intervals of these estimations. The peaks of z and x detected are used by module BPE to estimate the mass transit time (MTT). Similar to PPD module, in addition to the specified input signals, an implicit signal corresponding to the temporal info accompanies the other input signals. The BPE module computes A as distance between the corresponding peaks detected in z and x and verifies that A and is a valid MTT when put in context of previously estimated MTT. The results from this module is fed as the final output signal to the user interface.

Embodiments within the scope of the disclosure may also include non-transitory computer-readable storage media or machine-readable medium for carrying or having computer-executable instructions or data structures stored thereon. Such non-transitory computer-readable storage media or machine-readable medium may be any available media that can be accessed by a general purpose or special purpose computer. By way of example, and not limitation, such non-transitory computer-readable storage media or machine-readable medium can comprise RAM, ROM, EEPROM, CD-ROM or other optical disk storage, magnetic disk storage or other magnetic storage devices, or any other medium which can be used to carry or store desired program code means in the form of computer-executable instructions or data structures. Combinations of the above should also be included within the scope of the non-transitory computer-readable storage media or machine-readable medium.

Embodiments may also be practiced in distributed computing environments where tasks are performed by local and remote processing devices that are linked (either by hard-wired links, wireless links, or by a combination thereof) through a communications network.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

While the foregoing has been described with reference to various embodiments, it will be understood that these embodiments are illustrative and that the scope of the disclosure is not limited to them. Many variations, modifications, additions, and improvements are possible. More generally, embodiments in accordance with the patent have been described in the context or particular embodiments. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A vital signs monitoring system configured to be worn or carried on a body of a person, the system comprising:
at least one accelerometer configured to detect at least one vital sign parameter in a person and to output sensor signals indicative of the at least one vital sign parameter, the sensor signals having at least two axes; and
a processor configured to:
detect a peak pattern in the sensor signals and output a peak prediction signal according to a peak prediction algorithm, the peak prediction algorithm being configured to detect the peak pattern based on (i) the sensor signals, (ii) a context signal, and (iii) a concept drift signal, using probability density functions of the at least two axes of the sensor signals;
estimate a vital sign based on the peak prediction signal;
receive an input indicating environmental conditions and activity levels of the person;
detect, based on the input, changes in the environmental conditions and the activity levels of the person and output the context signal indicating the changes in the environmental conditions and the activity levels of the person; and
detect drift in the estimated vital sign and output the drift signal indicating the drift, the drift including changes in at least one of (i) the probability density functions of the at least two axes of the sensor signals, (ii) a joint probability of the at least two axes of the sensor signals, and (iii) a distribution of the peak pattern.

2. The system of claim 1, wherein the drift signal is provided to a sensor calibration system, the sensor calibration system being configured to calibrate the at least one accelerometer based on the drift signal.

3. The system of claim 1, wherein the processor is configured to receive the input indicating the environmental conditions and the activity levels via a user interface.

4. The system of claim 1, wherein the vital sign is blood pressure.

5. The system of claim 1, wherein the at least one accelerometer is configured to detect at least one or more of electrocardiogram (ECG) signal, a first motion signal, a second motion signal, a photoplethysmogram (PPG) signal, seismocardiogram signal (SCG) and ballistocardiogram (BCG) signal.

6. The system of claim 1, wherein, using the peak prediction algorithm, the processor is configured to identify peaks indicating exact timestamps when the heart of the person contracts and/or when blood rushes through the Aorta of the heart.

7. The system of claim 1, wherein the processor is configured to detect the drift using a hierarchical linear four rates approach.

8. A method of monitoring vital signs of a person, the method comprising:
- detecting at least one vital sign parameter in the person using at least one accelerometer, the at least one vital sign parameter having at least two axes;
- generating a peak prediction signal based on the detected vital sign parameter according to a peak prediction algorithm using a processor, the peak prediction algorithm being configured to detect the peak pattern based on (i) the detected vital sign parameter, (ii) a context signal, and (iii) a concept drift signal, using probability density functions of the at least two axes of the detected vital sign parameter;
- estimating a vital sign of the person based on the peak prediction signal using the processor;
- outputting an estimated vital sign signal;
- receiving an input indicating environmental conditions and activity levels of the person;
- generating a context signal indicative of changes in the environmental condition and the activity levels of the person detected using the processor; and
- generating a drift signal indicative of drift detected in the estimated vital sign signal using the processor, the drift including changes in at least one of (i) the probability density functions of the at least two axes of the sensor signals, (ii) a joint probability of the at least two axes of the sensor signals, and (iii) a distribution of the peak pattern.

9. The method of claim 8, further comprising:
- supplying the drift signal to a sensor calibration system; and
- calibrating the at least one accelerometer based on the drift signal.

10. The method of claim 8, further comprising:
- receiving the input indicating the environmental conditions and the activity levels of the person via a user interface.

11. The method of claim 8, wherein the vital sign is blood pressure.

12. The method of claim 8, wherein the at least one accelerometer is configured to detect at least one or more of electrocardiogram (ECG) signal, a first motion signal, a second motion signal, a photoplethysmogram (PPG) signal, seismocardiogram signal (SCG) and ballistocardiogram (BCG) signal.

13. The method of claim 8, wherein the peak prediction algorithm is configured to identify peaks indicating exact timestamps when the heart of the person contracts and/or when blood rushes through the Aorta of the heart.

14. The method of claim 8, wherein the drift is detected using a hierarchical linear four rates approach.

* * * * *